US008491927B2

(12) United States Patent
Epner et al.

(10) Patent No.: US 8,491,927 B2
(45) Date of Patent: *Jul. 23, 2013

(54) PHARMACEUTICAL COMPOSITION CONTAINING A HYPOMETHYLATING AGENT AND A HISTONE DEACETYLASE INHIBITOR

(75) Inventors: Elliot M. Epner, Harrisburg, PA (US); Luke M. Vaughan, Del Mar, CA (US)

(73) Assignee: Nimble Epitech, LLC, Del Mar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/769,913

(22) Filed: Apr. 29, 2010

(65) Prior Publication Data

US 2011/0129521 A1   Jun. 2, 2011

Related U.S. Application Data

(60) Provisional application No. 61/320,083, filed on Apr. 1, 2010, provisional application No. 61/301,956, filed on Feb. 5, 2010, provisional application No. 61/283,305, filed on Dec. 2, 2009.

(51) Int. Cl.
*A61K 9/70*   (2006.01)
*A61F 13/00*   (2006.01)
*A01N 43/04*   (2006.01)

(52) U.S. Cl.
USPC .............................................. 424/449; 514/46

(58) Field of Classification Search
USPC .............................................. 424/449; 514/46
See application file for complete search history.

(56) References Cited

U.S. PATENT DOCUMENTS

| 6,417,229 | B1 | 7/2002 | Sahagan et al. |
| 7,276,228 | B2 | 10/2007 | DiMartino |
| 7,538,135 | B2 | 5/2009 | Vedananda |
| 7,582,782 | B2 | 9/2009 | Baeschlin et al. |
| 7,652,061 | B2 | 1/2010 | Ksander et al. |
| 2002/0009487 | A1 | 1/2002 | Murdock et al. |

(Continued)

FOREIGN PATENT DOCUMENTS

| EP | 1 949 898 | 11/2005 |
| WO | WO03/024442 | 3/2003 |

(Continued)

OTHER PUBLICATIONS

International Search Report dated Sep. 17, 2010 issued in copending PCT Application No. PCT/US2010/01287.

(Continued)

*Primary Examiner* — Aradhana Sasan
(74) *Attorney, Agent, or Firm* — Lathrop & Gage LLP; Sean M. Coughlin, Esq.

(57) ABSTRACT

A pharmaceutical composition for induction therapy which has a hypomethylating agent and a histone deacetylase inhibitor ("HDAC inhibitor"); wherein the hypomethylating agent is a DNA and histone methylation inhibitor such as cladribine and the HDAC inhibitor is, for example, entinostat, panobinostat, vorinostat, and/or romedepsin; further wherein the hypomethylating agent and the HDAC inhibitor are combined in formulations for various administrations including e.g., a continuous delivery system such as a transdermal patch of at least one reservoir or a plurality of reservoirs, oral, a fixed-dose oral combination, intravenous, and combinations thereof. This pharmaceutical composition for induction therapy is used with a monoclonal antibody in the treatment of various cancers, sarcomas, and other malignancies.

16 Claims, 5 Drawing Sheets

U.S. PATENT DOCUMENTS

| | | | |
|---|---|---|---|
| 2004/0010001 | A1 | 1/2004 | Au |
| 2005/0059682 | A1 | 3/2005 | Rubinfeld |
| 2005/0119217 | A1 | 6/2005 | LaCasse et al. |
| 2007/0072796 | A1 | 3/2007 | Phiasivongsa et al. |
| 2007/0197957 | A1 | 8/2007 | Hunter et al. |
| 2007/0207186 | A1 | 9/2007 | Scanlon et al. |
| 2007/0281934 | A1* | 12/2007 | Buggy et al. ............ 514/235.2 |
| 2009/0252742 | A1 | 10/2009 | Bergstein |
| 2009/0286752 | A1 | 11/2009 | Etter et al. |
| 2010/0069458 | A1 | 3/2010 | Atadja et al. |
| 2010/0075915 | A1 | 3/2010 | Yu et al. |
| 2010/0093614 | A1 | 4/2010 | Hofland |

FOREIGN PATENT DOCUMENTS

| | | |
|---|---|---|
| WO | WO2005/065668 A2 | 7/2005 |
| WO | WO 2007/064945 | 6/2007 |
| WO | WO2007/109178 A2 | 9/2007 |
| WO | WO 2008/082646 | 7/2008 |
| WO | WO2008/116163 A1 | 9/2008 |
| WO | WO 2009/055343 | 4/2009 |
| WO | WO 2009/067543 | 5/2009 |
| WO | WO 2009/139888 | 11/2009 |
| WO | WO 2009/155477 | 12/2009 |
| WO | WO 2010/020787 | 2/2010 |

OTHER PUBLICATIONS

Taylor, Shirley M; "p53 and deregulation of DNA methylation in cancer"; Cell Science; vol. 2, No. 3; 2006.

Galm O. et al.; "Beyond Genetics—The Emerging Role of Epigenetic Changes in Hematopoietic Malignancies"; International Journal of Hematology vol. 80, No. 2 / Aug. 2004;http://www.ncbi.nlm.nih.gov/pubmed/15481439; Medizinische Klinik IV, Universitaetsklinikum Aachen; Cancer Epigenetics Laboratory, Molecular Pathology Program, Spanish National Cancer Centre.

Debby M.E.I. Hellebrekers et al.; "Dual Targeting of Epigenetic Therapy in Cancer"; Jan. 2007, pp. 76-91 Biochimica et Biophysica Acta (BBA)—Reviews on Cancer; vol. 1775, Issue 1 http://www.ncbi.nlm.nih.gov/pubmed/16930846.

Sugimoto T. et al.; "Escape Mechanisms from Antibody Therapy To Lymphoma Cells: Downregulation of CD20 Mrna by Recruitment of The HDAC Complex and Not by DNA Methylation" ;Biochem Biophys Res Commun. Dec. 4, 2009; 390(1):48-53. Epub Sep. 19, 2009. http://www.ncbi.nlm.nih.gov/pubmed/19769942; Department of Hematology and Oncology, Nagoya University Graduate School of Medicine.

Heller G. et al.; "Genome-Wide Transcriptional Response To 5-Aza-2'-Deoxycytidine And Trichostatin A in Multiple Myeloma Cells"; Cancer Res. Jan. 1, 2008; 68(1):44-54 http://www.ncbi.nlm.nih.gov/pubmed/18172295; Division of Oncology, Department of Medicine I, Medical University of Vienna.

Yuning Xiong et al.; "Histone Deacetylase Inhibitors Decrease DNA Methyltransferase-3B Messenger RNA Stability and Down-Regulate De Novo DNA Methyltransferase Activity in Human Endometrial Cells"; *Cancer Research* 65, 2684-2689, Apr. 1, 2005 http://www.ncbi.nlm.nih.gov/pubmed/15805266; Departments of [1]Obstetrics and Gynecology, Experimental Pathology, Internal Medicine, Division of Endocrinology, and[4] Biochemistry and Molecular Biology, Mayo Clinic and Foundation, Rochester, Minnesota.

Poulaki V. et al.; "Human Retinoblastoma Cells Are Resistant to Apoptosis Induced by Death Receptors: Role of Caspase-8 Gene Silencing"; Invest Ophthalmol Vis Sci. Jan. 2005; 46(1):358-66 http://www.ncbi.nlm.nih.gov/pubmed/15623796; Massachusetts Eye and Ear Infirmary, Harvard Medical School, Boston.

Picard V.; et al.; "MAGE-A9 Mrna and Protein Expression in Bladder Cancer"; Int J Cancer. May 15, 2007;120(10):2170-7 http://www.ncbi.nlm.nih.gov/pubmed/17290406; Centre de recherche en cancérologie de l'Université Laval, L'Hôtel-Dieu de Québec, Centre Hospitalier Universitaire de Québec.

Elias Jabbour et al.; "New Agents in Myelodysplastic Syndromes"; Current Hematologic Malignany Reports; 2005 http://www.ncbi.nlm.nih.gov/pubmed/15865871; Department of Leukemia, Unit 428, MD Anderson Cancer Center.

Smolewski P. et al.; "Proapoptotic Activity of Alemtuzumab Alone and in Combination with Rituximab or Purine Nucleoside Analogues in Chronic Lymphocytic Leukemia"; Leuk Lymphoma. Jan. 2005; 46(1):87-100 http://www.ncbi.nlm.nih.gov/pubmed/15621786; Department of Hematology, Medical University of Lodz and Copernicus Memorial Hospital Lodz, Poland.

L Nolan et al.; "Will Histone Deacetylase Inhibitors Require Combination with other Agents to Fulfil their Therapeutic Potential?"; British Journal of Cancer (2008);99, 689-694; http://www.nature.com/bjc/journal/v99/n5/full/6604557a.html; Cancer Research UK Clinical Centre, School of Medicine, University of Southampton.

Johnson et al.; "Advances in the Therapy of Chronic Lymphocytic Leukemia"; Current Opinion in Hematology; Jul. 2003—vol. 10—Issue 4—pp. 297-305.

Abbott BL.; "Advances in the Diagnosis and Treatment of Chronic Lymphocytic Leukemia"; Clin Adv Hematol Oncol. Jul. 2004;2(7):448-54; Department of Medicine, University of Missouri.

Else M. et al.; "The Role of Rituximab in Combination With Pentostatin or Cladribine for the Treatment of Recurrent/Refractory Hairy Cell Leukemia"; Cancer. Nov. 15, 2007; 110(10):2240-7. Section of Haemato-Oncology, Royal Marsden Hospital/Institute of Cancer Research.

Lamanna N.; "Advances in the Treatment of Chronic Lymphocytic Leukemia"; Curr Oncol Rep. Sep. 2005; 7(5):333-8.; Leukemia Service, Department of Medicine, Memorial Sloan-Kettering Cancer Center.

Lauria F. et al.; "Combination Therapies to Improve the Long-Term Outcome in Hairy Cell Leukemia"; Leuk Lymphoma. Oct. 2009; 50 Suppl 1:18-22; Department of Hematology and Transplant, University of Siena.

Kobayashi Y. et al.; "Combination Therapy With Rituximab and Cladribine for Patients With Follicular Lymphoma"; Gan To Kagaku Ryoho. Oct. 2007; 34(10):1623-7.; Dept. of Hematology and Immunology, Kyoto Second Red Cross Hospital.

Watanabe T. et al.; "Complete Response in a Patient With Colonic Mantle Cell Lymphoma With Multiple Lymphomatous Polyposis Treated With Combination Chemotherapy Using Anti-CD20 Antibody and Cladribine"; Gut. Mar. 2007;56(3):449-50.

Liu WB.; et al. "Dynamic Changes in DNA Methylation During Multistep Rat Lung Carcinogenesis Induced by 3-Methylcholanthrene and Diethylnitrosamine"; Toxicol Lett. Aug. 25, 2009; 189(1):5-13. Epub May 3, 2009; Department of Hygienic Toxicology, Preventive Medical College, Third Military; Medical University, Key Laboratory of Medical Protection for Electromagnetic; Radiation, Ministry of Education of China, Chongqing 400038, PR China.

Inwards DJ. et al.; "Long-Term Results of the Treatment of Patients With Mantle Cell Lymphoma With Cladribine (2-CDA) Alone (95-80-53) or 2-CDA and Rituximab (N0189) in the North Central Cancer Treatment Group"; Cancer. Jul. 1, 2008;113(1):108-16; Division of Hematology, Mayo Clinic.

Weiss MA.; "Novel Treatment Strategies in Chronic Lymphocytic Leukemia"; Curr Oncol Rep. May 2001; 3(3):217-22.; Leukemia Service, Department of Medicine, Memorial Sloan-Kettering Cancer Center.

Robak T. et al.; "Rituximab Combined With Cladribine or With Cladribine and Cyclophosphamide in Heavily Pretreated Patients With Indolent Lymphoproliferative Disorders and Mantle Cell Lymphoma"; Cancer. Oct. 1, 2006;107(7):1542-50; Department of Hematology, Medical University of Lodz, Copernicus Memorial.

Robak T. et al.; "Rituximab Plus Cladribine With or Without Cyclophosphamide in Patients With Relapsed or Refractory Chronic Lymphocytic Leukemia"; Eur J Haematol. Aug. 2007; 79(2):107-13; Department of Hematology, Medical University of Lodz and Copernicus Memorial.

Tsujimura A. et al.; "Successful Salvage Therapy With Cladribine and Rituximab for a Patient With a Relapsed Asian Variant of Intravascular Large B-Cell Lymphoma"; Rinsho Ketsueki. Oct. 2006; 47(10):1387-92; Department of Hematology, Japanese Red Cross Nagoya First Hospital.

Johnson SA. et al.; "Therapeutic Potential of Purine Analogue Combinations in the Treatment of Lymphoid Malignancies"; Hematol Oncol. Dec. 2000;18(4):141-153; Department of Haematology, Taunton & Somerset Hospital.

Extended European Search Report, EP10834854, issued Apr. 18, 2013.

* cited by examiner

PHARMACEUTICAL COMPOSITION CONTAINING A HYPOMETHYLATING AGENT AND A HISTONE DEACETYLASE INHIBITOR

CROSS REFERENCE TO RELATED APPLICATIONS

The present application claims priority to U.S. Provisional patent application No. 61/320,083 filed Apr. 1, 2010 and U.S. Provisional patent application No. 61/301,956 filed Feb. 5, 2010 and U.S. Provisional Application No. 61/283,305 filed Dec. 2, 2009; the entire disclosures of which are hereby incorporated by reference in their entirety.

STATEMENT OF RIGHTS TO INVENTIONS MADE UNDER FEDERALLY SPONSORED RESEARCH AND DEVELOPMENT

Not applicable.

TECHNICAL FIELD

Embodiments of the present invention relate to the field of pharmaceutical compositions containing a hypomethylating agent and a histone deacetylase inhibitor for induction therapy used with monoclonal antibody treatment of various cancers, sarcomas, and other malignancies.

BACKGROUND

The evolution of therapies for diseases associated with abnormal cell proliferation such as cancer has provided many choices in therapeutics agents for clinical treatment. To date, thousands of potential anticancer agents have been evaluated but the mainstay of treatments remains weighed down with complications and toxic side effects. Current therapeutic agents are categorized into six general groups: alkylating agents, antibiotic agents, antimetabolic agents, hormonal agents, plant-derived agents, and biologic agents. For a complete description of these agents, see U.S. Pat. No. 6,905,669.

Monoclonal antibody ("mAB") drugs are a relatively new innovation in biologic agents used in cancer treatment. A monoclonal antibody is a laboratory-produced molecule that is designed to attach to specific cancer cells. A few examples of mAB treatment include: rituximab—for chronic lymphocytic leukemia and non-Hodgkin's lymphoma; gemtuzamab for certain types of acute myelogenous leukemia; cetuximab—for head, neck and colon cancer; and alentuzumab—for T cell leukemias and lymphomas. Although promising as a treatment for cancers, the use of mABs as a stand alone treatment has failed to meet expectations. Therefore, monoclonal antibodies are most often supplemented with the use of highly toxic chemotherapy and radiation therapy to improve the patient survival rate. Clearly a need still exists for more effective drug system and administration regimens for treating cancer in a relatively nontoxic and specific manner.

SUMMARY OF THE DISCLOSURE

The present disclosure relates to embodiments of a relatively non-toxic pharmaceutical composition that combines a hypomethylating agent, specifically, a DNA and histone methylation inhibitor, with a histone deacetylase inhibitor ("HDAC inhibitor" or "HDACi") to provide a pretreatment ("induction therapy") for mAB treatment of various cancers, sarcomas, and other malignancies. Embodiments of the composition combine a hypomethylating agent (e.g., cladribine) and an HDAC inhibitor (e.g., entinostat, panobinostat, and vorinostat). The hypomethylating agent and the HDAC inhibitor may be combined in formulations for various administrations e.g., a continuous delivery system such as a transdermal patch of at least one reservoir or a plurality of reservoirs, oral, a fixed-dose oral combination, intravenous, and combinations thereof. Induction therapy that combines a hypomethylating agent and an HDAC inhibitor results in an unexpected and dramatic increase in the efficacy of mAB treatment of cancers, sarcomas, and various other malignancies. These and other advantages of the invention will be further understood and appreciated by those skilled in the art by reference to the following written description, claims and appended drawings.

BRIEF DESCRIPTION OF THE DRAWINGS

Embodiments of the present invention will be readily understood by the following detailed description in conjunction with the accompanying drawings.

DETAILED DESCRIPTION OF DISCLOSED EMBODIMENTS

Figure 1:
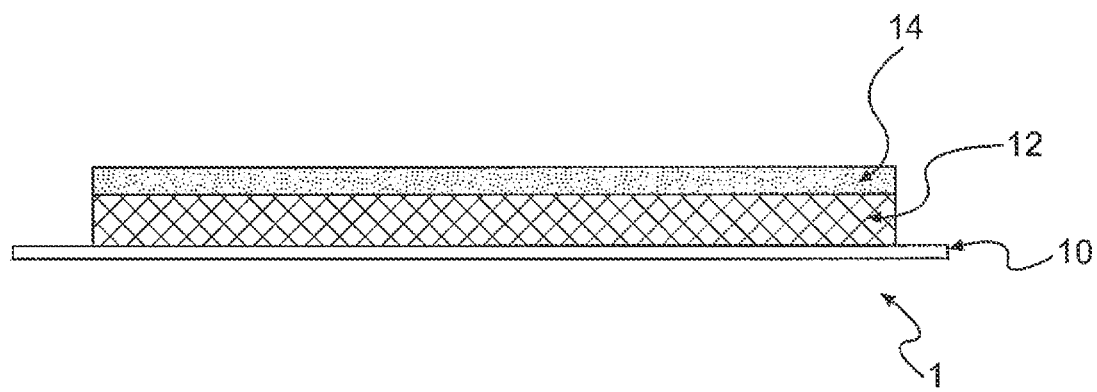
FIG. 1 illustrates a side view of a monolithic patch construction.

In the following detailed description, reference is made to the accompanying drawings that form a part hereof, and illustrate embodiments in which the invention may be practiced. The description may use the phrases "in an embodiment," or "in embodiments," which may each refer to one or more of the same or different embodiments. In addition, various operations may be described as multiple discrete operations in turn, which may be helpful in understanding embodiments of the present invention. However, the order of description should not be construed to imply that these operations are order dependent. It is to be understood that other embodiments may be used and structural or logical changes may be made without departing from the scope of the present invention. Therefore, the following detailed description is not intended to be limiting.

Epigenetics is the study of inherited changes in phenotype or gene expression caused by mechanisms other than changes in the underlying DNA sequence. These changes may remain through cell divisions for the remainder of the cell's life and may also last for multiple generations. However, there is no change in the underlying DNA sequence of the organism; instead, non-genetic factors cause the organism's genes to behave or express themselves differently.

DNA methylation is an epigenetic modification of cytosine that is important for silencing gene transcription. Genomic methylation patterns, which remain generally stable in the adult, become profoundly altered in most human tumors. (Smet, C. D.; et al., *DNA hypomethylation in cancer: Epigenetic scars of a neoplastic journey*, Epigenetics, 5(3):206-13 (2010)). Additionally, epigenetics has a demonstrated and important role in B cell malignancies. (Debatin, K., et al. *Chronic lymphocytic leukemia: keeping cell death at bay*, Cell, 129(5):853-5, (2007); Martin-Subero, J., *Towards defining the lymphoma methylome*. Leukemia, 20(10):1658-60. (2006)).

Cladribine, also known as 2CdA, acts as a DNA hypomethylating agent. (Wyczechowska, D. et al., *The effects of cladribine and fludarabine on DNA methylation in K562 cells*, Biochem Pharmacol, 65:219-225 (2003); Yu, M. K., et al., *Epigenetics and chronic lymphocytic leukemia*, Am J Hematol., 81(11):864-9 (2006)). More specifically, cladribine is a deoxyadenosine analogue with substitution of a hydrogen atom with chlorine at the 2-position of the purine ring. Other purine analogs include fludarabine, pentostatin and clofarabine. Like fludarabine, pentostatin, and clofarabine, cladribine is a purine nucleoside analog anti-metabolite with selective toxicity towards lymphocytes and monocytes. Given its lymphotoxic effects, cladribine has been developed for the treatment of hematologic malignancies, primarily lymphoid malignancies, and inflammatory conditions. Currently, cladribine is FDA approved for the treatment of hairy cell leukemia.

Unlike other purine nucleoside analogues, cladribine's ability to interfere with DNA synthesis and repair allows for cytotoxicity against both resting and dividing lymphocytes. Given that indolent lymphoid malignancies are characterized by having a significant proportion of cells that are in the G0 phase of the cell cycle, e.g. the resting phase, cladribine has shown therapeutic promise in treating these malignancies.

Excellent clinical activity is observed with cladribine and rituximab, a mAB against the protein CD20, in combination therapy for mantle cell lymphoma, e.g.: 52% complete remission rate with 80% in complete remission at median of 22 months. (Inwards, D. J. et al., *Long-term results of the treatment of patients with mantle cell lymphoma with cladribine (2-CDA) alone (95-80-53) or 2-CDA and rituximab (N0189) in the North Central Cancer Treatment Group*. Cancer, 113 (1):108-16 (2008)). In another on-going study, results indicate 60% complete remission rate with 93% in complete remission at median of 25 months. (Oregon Health and Science University: Clinical trials—manuscript in preparation.) This manuscript is a retrospective, IRB approved review of patients treated with cladribine rituximab combinations since 1998. Moreover, cladribine in combination with rituximab may treat chronic lymphocytic leukemia ("CLL") and mantle cell leukemia ("MCL"), as disclosed in WO 2008/116163 and WO 2007/067695, the entire disclosures of which are hereby incorporated by reference in their entireties.

There is also a newly discovered second mechanism of action of cladribine. Specifically cladribine has been shown to inhibit histone methylation. (Spurgeon, S. et al, *Cladribine: not just another purine analogue?* Expert Opin. Investig. Drugs, 18(8):1169-1181, (2009); Epner, E., *The epigenetics of mantle cell lymphoma*, Abstract, 2010 Mantle Cell Lymphoma Workshop, Lymphoma Research. Foundation, March (2010)). Evidence also exists that DNA methylation and histone methylation are linked, and inhibition of both processes may be necessary for effective, permanent reversal of gene silencing in cancer cells. (Cedar, H. et al., *Linking DNA methylation and histone modification: patterns and paradigms*, Nature Reviews Genetics 10:295-304 (2009)). Therefore, cladribine is a hypomethylating agent that inhibits both DNA and histone methylation.

It has also been shown that HDAC inhibitors plus DNA hypomethylation may be additive in successful treatment of various cancers and other malignancies. (Cameron, E. E. et al., *Synergy of demethylation and histone deacetylase inhibition in the re-expression of genes silenced in cancer*, Nat Genet, (1999); Garcia-Manero, G., et al. *Phase ½ study of the combination of 5-aza-2'-deoxycytidine with valproic acid in patients with leukemia*, Blood, November 15; 108(10):3271-9 (2006)). Combinations of HDACi with azacytidine, deoxyazacytidine, and purine analogues have been studied in vitro and in clinical trials for a variety of malignancies, particularly in myelodysplasia ("MDS") and acute myeloid leukemia ("AML"). (Bouzar A. B., et al., *Valproate synergizes with purine nucleoside analogues to induce apoptosis of B-chronic lymphocytic leukaemia cells*, Br. J. Haematol., 144(1):41-52 (2009); Gore S. D., et al., *Combination DNA methyltransferase and histone deacetylase inhibition in the treatment of myeloid neoplasms*, Cancer Res., 66:6361-9 (2006); Soriano A, et al., *Safety and clinical activity of the combination of 5-azacytidine, valproic acid, and all-trans retinoic acid in acute myeloid leukemia and myelodysplastic syndrome*, Blood. 110:2302-8 (2007)). Additional insight into at least one HDAC inhibitor, vorinostat, indicates translation of cyclin D1 in mantle cell lymphoma is inhibited. (Kawamata, N. et al., *Suberoylanilide hydroxamic acid (SAHA; vorinostat) suppresses translation of cyclin D1 in mantle cell lymphoma cells*, Blood, 110(7):2667-73 (2007)).

The most common administration of 2CdA and HDAC inhibitors is intravenous. Continuous administration of both 2CdA and HDACi is often optimal. There is both scientific and clinical rationale for the continuous delivery of cladribine and other epigenetic drugs to achieve maximum efficacy. (Huynh, E. et al., *Cladribine in the treatment of hairy cell leukemia: initial and subsequent results*, Leukemia & Lymphoma, 50(s1):12-17 (2009)). As a result, administration of either or both 2CdA and HDACi often require long hospital stays of 5-6 days in repeated in cycles. Cycles may be as often as once a month for 6-8 months depending on the treatment protocol prescribed and patient health. To overcome the cost and inconvenience of long hospital stays, a newly developed embodiment contemplates a continuous delivery system such as through a transdermal patch. In addition, therapeutic efficacy and permanent reversal of gene silencing in cancer may be optimally achieved by continuous infusion of epigenetic drugs that target histone methylation, DNA methylation, and histone acetylation.

Transdermal Device Construction Options

Transdermal delivery of 2CdA and HDACi prior to mAB treatment is attractive because it provides a mechanism for continuous administration of drugs while not confining the patient to the hospital or immobilizing the patient as with intravenous delivery of drugs. Generally speaking, the main parts of a transdermal patch are: a liner to protect the patch during storage—the liner is removed prior to use; a composition or drug in solution that is in direct contact with the release liner; an adhesive that adheres the parts of the patch together and adheres the patch to the skin; a membrane that controls the release of the drug from a reservoir and/or multi-layer patches; and a backing that protects the patch from the outer environment. Embodiments of the transdermal device construction options include, but are not limited to, the following examples.

A monolithic (drug-in-adhesive) patch (1) (FIG. 1) includes a release liner (10); skin contact adhesive matrix (12) wherein the adhesive matrix contains for example, the drug, drug solubilizers, skin penetration enhancers, skin anti-irritants, crystallization inhibitors; ("transdermal composition"); and an occlusive backing film (14). In any case, penetration of the transdermal composition may also be enhanced by various forms of skin pre-treatment such as micro-needle poration, scrubbing off the stratum corneum, sonication, laser treatment, iontophoresis, inducing changes in composition polarity, and exothermic reactions that cause a patch to warm when exposed to air. Another embodiment, (not shown) is a multi-layer transdermal patch having multiple drug-in-adhesive matrixes that are layered one above the other wherein each layer is separated from the other, for example, by a membrane or heat seal. In a multi-layer transdermal patch each matrix layer is responsible for the releasing a transdermal composition.

Figure 2:
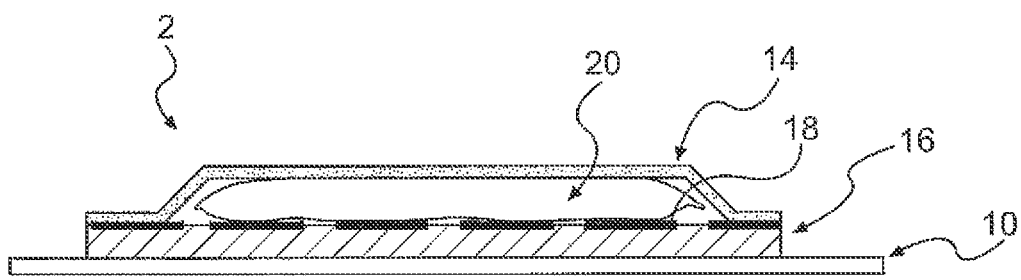
FIG. 2 illustrates a side view of a reservoir ("Ravioli") patch construction.

Another embodiment is shown in FIG. 2 as a reservoir patch ("Ravioli patch") (2) that includes a release liner (10), a skin contact adhesive (16), occlusive backing film (14) and a drug permeable membrane (18) in fluid communication with and forming a portion of a reservoir (20) that contains the transdermal composition wherein the drug permeable membrane (18) controls the release of the transdermal composition from the reservoir (20). Examples of a drug permeable membrane (18) include 9% EVA, a rate controlling membrane, or microporous membrane. The microporous membrane may have pores with diameters in the range of about 0.05 to about 10 micrometers (μm), preferably in the range of about 0.1 to about 6.0 μm.

Figure 3:
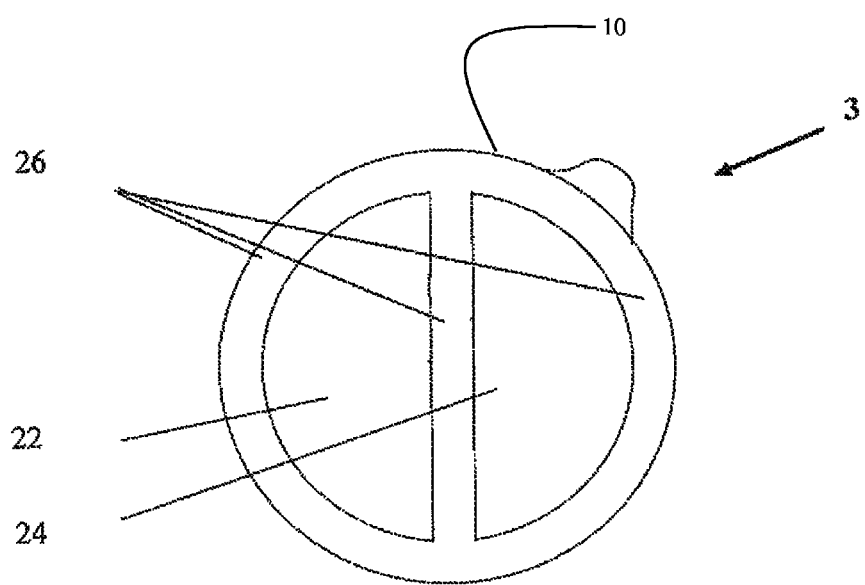
FIG. 3 illustrates a top view of a dual reservoir patch.

FIG. 3 illustrates a top view of an embodiment of a dual reservoir patch (3) with a circular construction with a release liner (10), two reservoirs—reservoir A (22) and reservoir B (24), and a heat seal (26) which is a permanent seal of the membrane and the occlusive backing providing necessary enclosure for the reservoirs and their separation. In other embodiments, a dual reservoir patch (3) may have reservoirs (22 and 24) arranged in a rectangular or concentric configuration. The reservoirs may be formed in a desired reservoir configuration based on the type and amount of drug required for desired dosage ratios wherein the reservoirs have different volume capacities.

Figure 4:
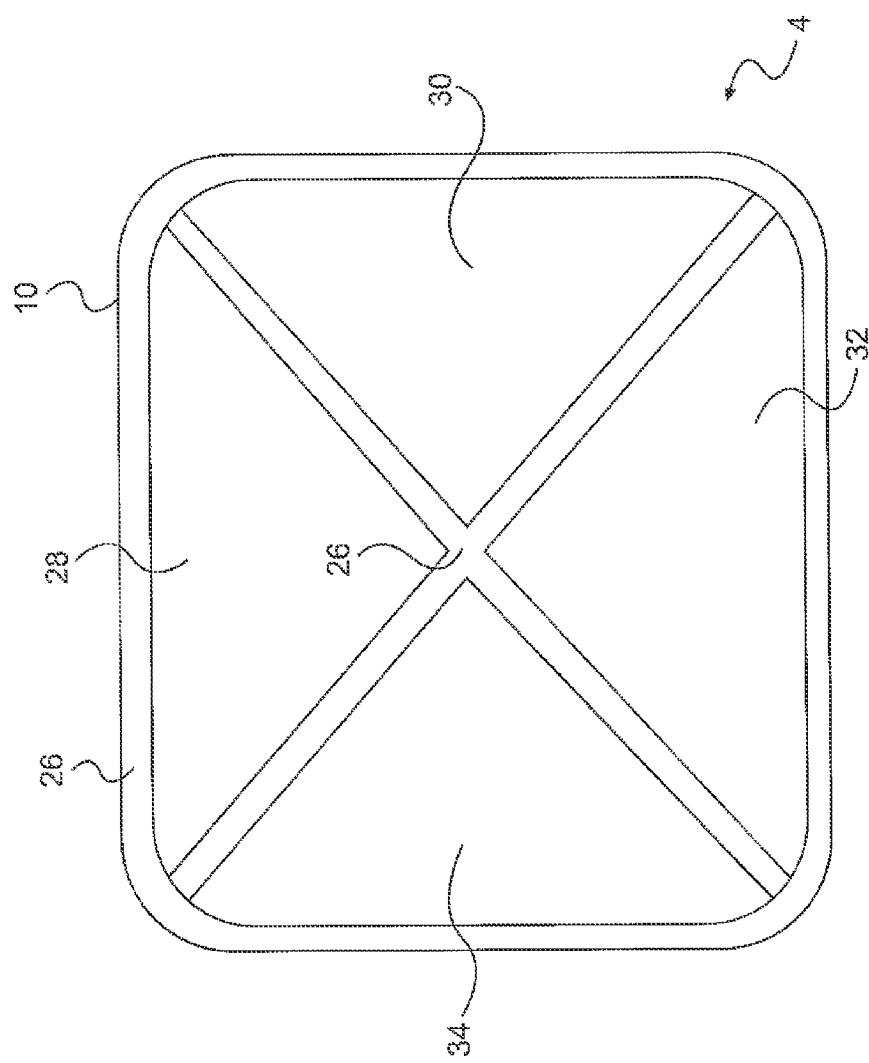
FIG. 4 illustrates a top view of a quadruplet reservoir patch.

In another embodiment, FIG. 4 illustrates a top view of a quadruplet reservoir patch (4) for simultaneous transdermal delivery of four transdermal compositions with a release liner (10), four reservoirs—reservoir A (28), reservoir B (30), reservoir C (32) and reservoir D (34), and a heat seal (26).

In another embodiment (not shown) the patch may have an occlusive backing (14) as in FIGS. 1 and 2 that extends over the reservoirs shown in FIGS. 2-4 that exceeds the borders of the reservoirs by a few centimeters. The purpose of an occlusive backing (14) that extends over the reservoirs is to secure the patch to skin for an extended period of time such as may be needed in a 1 to 5 day patch as described below.

Feasibility Study of 2CdA and HDACi

A feasibility study of transdermal delivery of cladribine and HDAC inhibitors was conducted using the Franz Cell Method. The scope of the ongoing study is to determine the passive transdermal diffusion rate (passive perfusion) of cladribine and multiple HDAC inhibitors for creation of continuous transdermal delivery for induction therapy.

By way of background, skin consists of three major layers: outer stratum corneum, underlying viable epidermis and next to it dermis. In transdermal drug delivery the transdermal composition that carries the drug or diffusing molecule must be in intimate contact with the skin's stratum corneum providing passage of the molecule from the transdermal composition into the stratum corneum. The diffusing molecules must overcome the diffusion resistance the patch membrane and the thermodynamics of partitioning between the transdermal composition and the stratum corneum. Diffusion is also governed by the size of the molecule and the $K_{ow}$, indicates molecular "ability" to transfer from one medium to another one, when both are in intimate contact. The higher value of $K_{ow}$ the more lipophilic the molecule is.

Molecules with log $K_{ow}$ values in range of 1-3, are most favorable to partition into the skin from weakly hydrophilic matrices such as hydrogels. Molecules with higher values of log $K_{ow}$>3 will typically show slower transdermal rates due to extreme decrease of their solubility in the hydrophilic epidermis. On the other hand, molecules of very low log $K_{ow}$<1, such as polar or ionized molecules, are practically insoluble in the stratum corneum and, therefore, their partition into the skin from any matrix is expected to be very low resulting in a very low transdermal flux. It is possible, however, to increase the solubility of the polar molecules in the stratum corneum by use of substances that affect the structure of the stratum corneum in such a way that the tight lipophilic structure of the stratum corneum open up allowing for polar molecules to pass through without too much resistance.

Experimental Work

A three-stage study was conducted. Cladribine and the HDAC inhibitor, entinostat, were tested first. Cladribine has 1>log $K_{ow}$>0, entinostat has log $K_{ow}$>2. The target systemic transdermal dose of cladribine was set for 1-2 mg/day. The target systemic transdermal dose of entinostat is set for 2-3 mg/day.

Cladribine was mixed with about 2 percent of a concentration of a thickener comprising a cellulose component to thicken the cladribine composition. This was repeated for entinostat. Thickeners for thixotropic compositions range from about 1 percent to about 5 percent. Other thickeners may include hydroxy methyl cellulose, hydroxylpropyl cellulose, hydroxylethyl cellulose polyacrylic acid, and/or, sodium carboxy methyl cellulose. Cladribine and entinostat were mixed into ethanol/water and other ethanol-based solutions until they were completely dissolved and then the hydroxymethyl cellulose was added and the solution was mixed until it became a homogeneous thixotropic mix.

All testing was performed in an incubator at 32 degrees Celsius. The porous membrane used had a 6.0 μm diameter pore that was evenly spaced throughout the membrane. The following liquid systems containing cladribine or entinostat, at saturation concentrations, were tested and provide sample embodiments for use in reservoir-patch constructions:

EXAMPLE 1

| | |
|---|---|
| Entinostat | 50 mg |
| Ethanol | 1 mL |
| Water | 0.5 mL |
| Hydroxy methyl cellulose | 15 mg |

EXAMPLE 2

| | |
|---|---|
| Cladribine | 23.9 mg |
| Ethanol | 0.5 mL |
| Water | 0.5 mL |
| Hydroxy methyl cellulose | 10 mg |

Second, additional in vitro tests were conducted to determine effect of application of some skin penetration enhancement on the transdermal flux using two enhancers: dimethyl sulfoxide ("DMSO") and oleic acid.

EXAMPLE 3

| | |
|---|---|
| Cladribine | 23.9 mg |
| Ethanol | 0.7 mL |
| Water | 0.7 mL |
| Hydroxy methyl cellulose | 10 mg |

EXAMPLE 4

| | |
|---|---|
| Cladribine | 19.4 mg |
| Ethanol | 0.5 mL |
| DMSO | 0.5 mL |
| Hydroxy methyl cellulose | 10 mg |

Third, in vitro transdermal flux was tested using human cadaver epidermis by the Franz Cell diffusion method. The reservoir patches were constructed with a microporous membrane of 0.6 μm and transdermal compositions containing cladribine or entinostat at saturation concentrations were placed inside of the reservoir and heat sealed. Round pieces of human cadaveric skin were cut out. The patches were placed on top of the skin and mounted in the Franz Cells between the donor compartment and the receiver compartments of the cell. The two compartments were tightened together with a screw-on pinch clamp. The cells were placed in the incubator at 32 degrees Celsius and the receiving phosphate buffer saline ("PBS") in the Franz Cell was tested for concentration of cladribine or entinostat that passed through the human cadaveric epidermis over a 24 hour time period.

Figure 5:
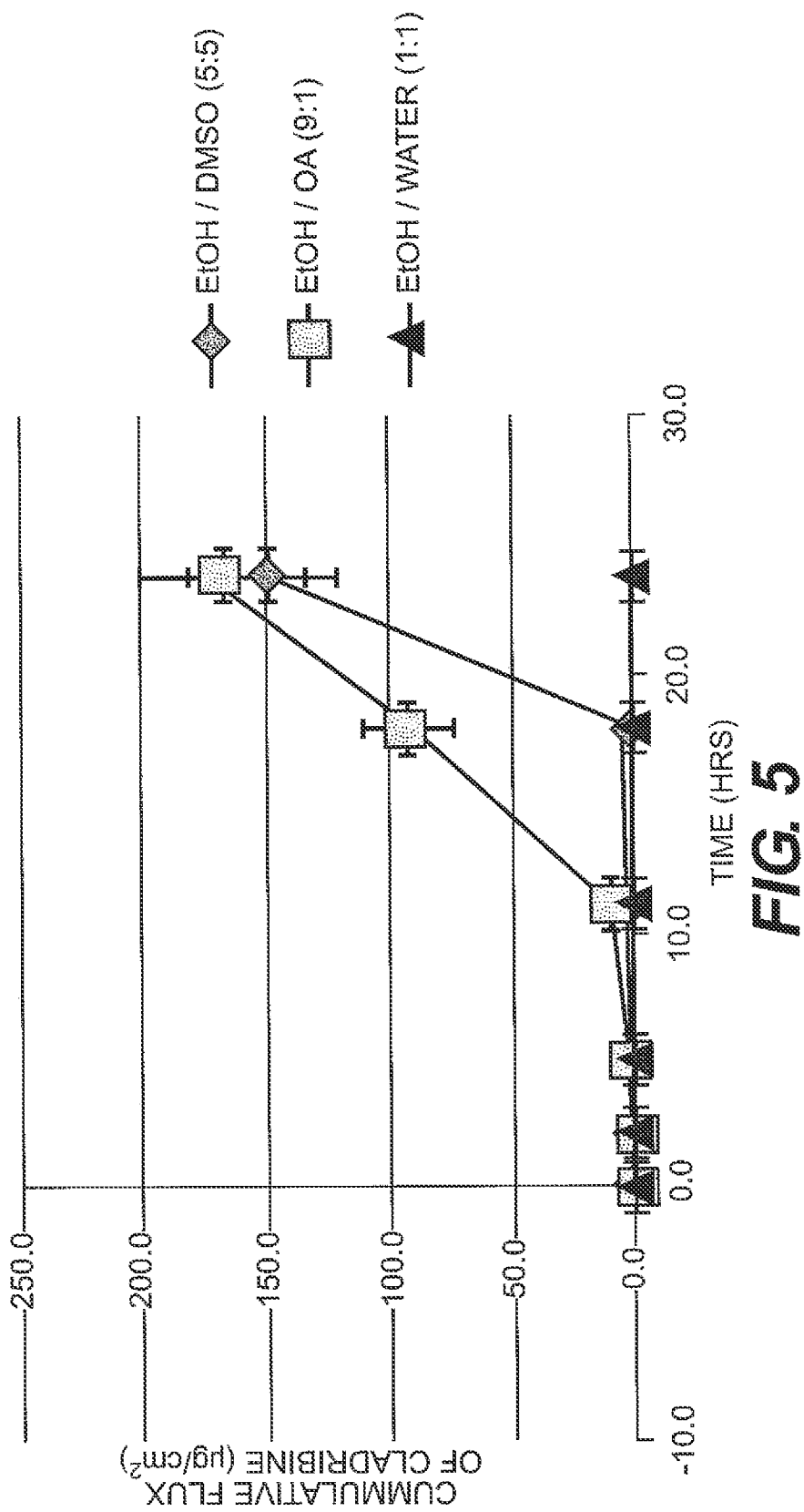
FIG. 5 illustrates kinetic profile of transdermal delivery of cladribine in vitro.
Figure 6:
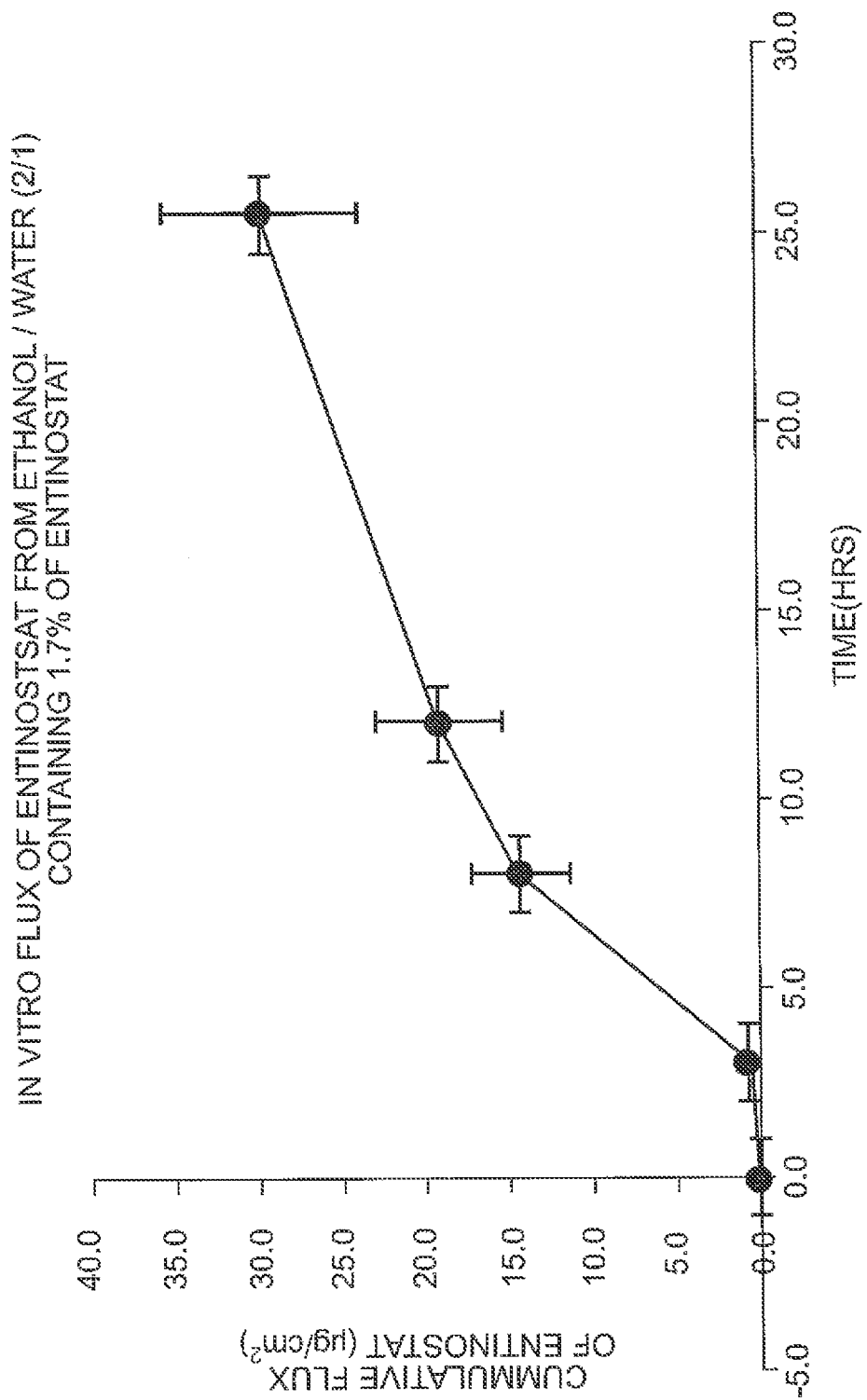
FIG. 6 illustrates kinetic profile of transdermal delivery of entinostat in vitro.

The results of transdermal flux were graphed as a function of time. (FIGS. 5, 6). As indicated by the graph in FIG. 5 the optimum transdermal flux of cladribine was 170 $\mu g/cm^2/day$ obtained from the patch containing cladribine saturated in ethanol/DMSO (50/50). After 10 hrs of a lag time, the cladribine transdermal delivery was sustained. The optimum transdermal flux of entinostat as indicated in FIG. 6 was 29 $\mu g/cm^2/day$ obtained from the patch containing entinostat saturated in ethanol/water (2/1); after 3 hrs of a lag time the transdermal delivery was sustained.

Various formulations of the composition, may allow for the use of a transdermal patch. The following are examples of proposed formulations for a transdermal patch delivery system.

EXAMPLE #5

| | |
|---|---|
| Cladribine or HDACi | 1-20 mg |
| Silicon adhesive | 80-99 mg (Bio PSA 7-3402) |
| Polyvinylpyrrolidon ("PVP") | 1-10 mg (Crystallization inhibitor) |

EXAMPLE #6

| | |
|---|---|
| Cladribine or HDACi | 1-40 mg |
| Duro-Tak 87-2677 | 60-99 mg (and any other acrylic adhesives) |
| PVP | 1-10 mg |
| Oleic Acid (enhancer) | 1-10 mg (or any other enhancer) |
| 1,2 Propylene Glycol | 10-20 mg (drug solubilizer) |

(Additional solubilizers such as glycols or polyglycols may be used)

EXAMPLE #7

| | |
|---|---|
| Cladribine or HDACi | 1-40 mg |
| Polyisobutylene (PIB) | 60-99 mg |
| PVP | 1-10 mg |
| Oleic Acid (enhancer) | 1-10 mg |
| 1,2 Propylene Glycol (drug solubilizer) | 10-20 mg |

The PIB in Example 7 above may also be substituted with any other rubber or acrylic hybrid adhesive.

Based on these results, in the single or multiple reservoir patch configurations, the transdermal composition may be a single drug-based composition of either a hypomethylating agent or an HDAC inhibitor. In other embodiments, the hypomethylating agent and HDAC inhibitor may be mixed to form an admixture. In an embodiment, a dual reservoir patch (3) may contain, for example, cladribine in a first reservoir (22) and entinostat in a second (24) reservoir. In another embodiment, a single reservoir patch (2) may contain, for example, cladribine and entinostat in a single reservoir (20).

In another embodiment, multiple hypomethylation drugs and multiple HDACi's may be used. Using a multi-reservoir patch as in FIG. 3 or 4, other pharmaceutical agents may be added to enhance the performance of cladribine and the HDACi individually or in combination. In another embodiment, when using the monolithic drug-in-adhesive patch shown in FIG. 1, two separate patches may be used—one with a hypomethylating agent and one with an HDACi.

The predicted transdermal dose of cladribine and some HDACi from saturated aqueous solutions are summarized in the table below.

| Drug | Molecular Weight | Log $K_{ow}$ | $K_p$ (cm/hr) | Water Solubility (mg/mL) | Transdermal Dose (mg/100 cm²/ 24 hrs) |
|---|---|---|---|---|---|
| Cladribine | 285.7 | 0.8 | 0.000133 | 3.1 | 1.3 |
| Romidepsin | 540.7 | 2.2 | 0.000042 | 0.005 | 0.003 |
| Entinostat | 376.4 | 2.0 | 0.000258 | 1.7 | 2.2 |
| Panobinostat | 349.4 | 3.0 | 0.00169 | 0.017 | 0.126 |

Dermal permeability coefficient $K_P$, water solubility and transdermal dose were calculated using a program developed by the U.S. Environmental Protection Agency and Syracuse Research Corporation.

In one embodiment, the delivered dosages for each of the drugs provided to the individual may be altered based on a variety of factors, including a determined safe and therapeutically effective dose, and the size, age, health, etc. of the patient. An effective dose of each of the delivered drugs thus depends on the particular individual treated. An "effective dose" may be considered to be the minimum dose that produces the desired effect. (W. K. Rasheed et al., *Histone deacetylase inhibitors in cancer therapy*, Expert Op. Invest. Drugs, 16(5):659-78 (2007)).

Patients may be treated with DNA and histone hypomethylating agents in combination with an HDACi as induction therapy for one or more cycles of mAB treatment for a specific cancer, sarcoma and or other malignancy wherein the mAB is specific to the targeted cancer, sarcoma, and/or malignancy. The administration and duration of induction therapy duration may be adjusted as needed to the cycles of mAB treatment. In one embodiment, a suitable mAB cycle duration may be 20-30 days, such as 28 days. In one treatment protocol, ten mAB cycles may be implemented. In another treatment protocol four to six mAB cycles may be implemented.

Presently, cladribine is the only known molecule that inhibits both DNA and histone methylation. As other hypomethylating agents are discovered, they may substitute for cladribine in the formulations described herein.

1-Day Patch

An effective dose of a hypomethylating agent such as cladribine and an HDACi such as entinostat may be delivered in a two-zone or multi-reservoir transdermal patch wherein the concentration of cladribine is about 5 to about 15 mg/m$^2$ and entinostat is about 10 to about 20 mg/m$^2$. At this dose the transdermal patch may comprise a "1-day patch" and may be administered every day for 5-7 days prior to the cycle of mAB treatment. In another embodiment of the 1-day patch, the concentration of cladribine is about 5 to about 15 mg/m$^2$ and the HDAC inhibitors, romidepsin or panobinostat, may substitute for entinostat at the same concentration of about 10 to about 20 mg/m$^2$.

5-Day Patch

In another embodiment, an effective dose of a hypomethylating agent such as cladribine and an HDACi such as entinostat may be delivered in a two-zone or multi-reservoir transdermal 5-day patch; wherein the concentration of cladribine is about 20 to about 100 mg/m$^2$ and entinostat is about 40 to about 80 mg/patch. At this dose the transdermal patch is administered once and removed 5 days later prior to the cycle of mAB treatment. In another embodiment of the 5-day patch the concentration of cladribine is about 20 to about 100 mg/m$^2$ and the HDAC inhibitors, romidepsin or panobinostat, may substitute for entinostat at about 40 to about 80 mg/m$^2$.

Intravenous

In another embodiment, an effective dose of a hypomethylating agent such as cladribine and an HDACi such as romidepsin are delivered intravenously ("iv"); wherein the concentration of cladribine is about 2 to about 5 mg/m$^2$ and romidepsin is about 8 to about 20 mg/m$^2$. It is contemplated that for each IV administration described herein, the hypomethylating agent and HDACi may be administered separately or in an admixture. At this dose the IV induction therapy is administered once a day for five days prior to the cycle of mAB treatment.

In another embodiment, an effective dose of a hypomethylating agent such as cladribine and an HDACi such as valproic acid is delivered intravenously; wherein the concentration of cladribine is about 2 to about 5 mg/m$^2$ and valproic acid is about 250 to about 1000 mg. At this dose the IV induction therapy is administered once a day for five days prior to the cycle of mAB treatment.

In another embodiment, an effective dose of a hypomethylating agent such as cladribine and an HDACi such as belinostat is delivered intravenously; wherein the concentration of cladribine is about 2 to about 5 mg/m$^2$ and belinostat is about 500 to about 1200 mg/m$^2$. At this dose the IV induction therapy is administered once a day for five days prior to the cycle of mAB treatment.

Oral Composition

In another embodiment, an effective dose of a hypomethylating agent such as cladribine and an HDACi such as vorinostat is delivered in an oral composition comprising a concentration of cladribine at about 5 to about 20 mg/m$^2$ and vorinostat at about 200 to about 400 mg. It is contemplated that for each oral administration described herein, the hypomethylating agent and HDACi may be administered individually or in a combination oral dose form e.g. a fixed-dose combination ("FDC"). An FDC is a formulation of two or more active ingredients such as but not limited to the hypomethylating agent and an HDACi combined in a single dosage form; different dose preparations are available within the parameters herein set forth. At this FDC the induction therapy may be administered orally once a day for five days prior to the cycle of mAB treatment.

In another embodiment, an effective dose of a hypomethylating agent such as cladribine and an HDACi, such as valproic acid, is delivered in an oral composition comprising a concentration of cladribine at about 5 to about 20 mg/m$^2$ and valproic acid at about 250 mg to about 500 mg. With this combination of drugs in the induction therapy, oral valproic acid may be administered three times a day for five days and cladribine may be administered once a day for five days prior to the requisite cycle of mAB treatment.

In another embodiment, an effective dose of a hypomethylating agent such as cladribine and an HDACi such as entinostat acid is delivered in an oral composition comprising a concentration of cladribine at about 5 to about 20 mg/m$^2$ and entinostat at about 5 to about 10 mg. In this form and at this dose the induction therapy is administered orally once a day for five days prior to the cycle of mAB treatment.

In another embodiment, an effective dose of a hypomethylating agent such as cladribine and an HDACi such as panobinostat is delivered in an oral composition comprising a concentration of cladribine at about 5 to about 20 mg/m$^2$ and panobinostat at about 10 to about 20 mg. At this FDC the induction therapy is administered orally once a day for five days prior to the cycle of mAB treatment.

The following table summarizes dosing combinations for embodiments of the present invention.

| Delivery Mode | HDACi | Administration Regimen | Hypomethylating Agent | Administration Regimen |
|---|---|---|---|---|
| | Romidepsin | | Cladribine | |
| 1-day patch | 10-20 mg/m$^2$ | Daily × 5 days | 5-15 mg/m$^2$ | Daily × 5 days |
| 5-day patch | 40-80 mg/m$^2$ | Once per 5 days | 20-100 mg/m$^2$ | Once per 5 days |
| IV | 8-20 mg/m$^2$ | Daily × 5 days | 2-5 mg/m$^2$ | Daily × 5 days |

-continued

| Delivery Mode | HDACi | Administration Regimen | Hypomethylating Agent | Administration Regimen |
|---|---|---|---|---|
| | Vorinostat | | Cladribine | |
| Oral | 200-400 mg Valproic Acid | Daily × 5 days | 5-20 mg/m$^2$ Cladribine | Daily × 5 days |
| Oral | 250-500 mg | Orally 3×/day | 5-20 mg/m$^2$ | Daily × 5 days |
| IV | 500-1000 mg Entinostat | Daily × 5 days | 2-5 mg/m$^2$ Cladribine | Daily × 5 days |
| 1-day patch | 10-20 mg/m$^2$ | Daily × 5 days | 5-15 mg/m$^2$ | Daily × 5 days |
| 5-day patch | 40-80 mg/m$^2$ | Once per 5 days | 20-100 mg/m$^2$ | Once per 5 days |
| Oral | 5-10 mg Belinostat | Daily × 5 days | 5-20 mg/m$^2$ Cladribine | Daily × 5 days D 1-5 |
| IV | 500-1200 mg/m$^2$ Panobinostat | Daily × 5 days | 2-5 mg/m$^2$ Cladribine | Daily × 5 days |
| 1-day patch | 10-20 mg/m$^2$ | Daily × 5 days | 5-15 mg/m$^2$ | Daily × 5 days |
| 5-day patch | 40-80 mg/m$^2$ | Once per 5 days | 20-100 mg/m$^2$ | Once per 5 days |
| Oral | 10-20 mg | Daily × 5 days | 5-20 mg/m$^2$ | Daily × 5 days |

Cladribine is readily available for topical, oral and IV formulations. Romidepsin is readily available for topical and iv formulations. Vorinostat is readily available for oral formulations. Valproic acid is readily available for oral and IV formulations. Entinostat is readily available for topical and oral formulations. Belinostat is readily available in intravenous formulations. Panobinostat is readily available for topical and oral formulations.

The combinations of hypomethylating agent and HDAC inhibitors presented are illustrative only. One of ordinary skill in the art can see that additional combinations of a hypomethylating agent and HDAC inhibitors can be created to meet the requirements of an individual and/or treatment protocol. Additionally, the above described induction therapy may be further enhanced by inclusion in the treatment regimen of one or more additional drugs, for example a proteasome inhibitor, such as bortezomib, and an mTOR (mammalian target of rapamycin) inhibitor.

The term "administration" and or "administered" as used herein includes e.g., topical, transdermal, parenteral, vaginal, rectal, ocular, transmucosal, intranasal, and intravenous. The term "topical" implies intradermal delivery. The term "transdermal" implies systemic delivery via passage through the skin. The term "parenteral" as used herein includes e.g., subcutaneous injections, intravenous, intramuscular, intracisternal injection, or infusion techniques. "Intravenous" means intradermal, intramuscular, intramammary, intraperitoneal, intrathecal, retrobulbar, and/or intrapulmonary injection. The term "pharmaceutically acceptable carrier" as used herein includes any and all solvents, dispersion media, coatings, antibacterial and antifungal agents, isotonic and absorption delaying agents and the like. The use of such media and agents for pharmaceutically active substances is well known in the art.

A transdermal composition may be formulated as a cream, salve, emollient, foam, lotion, liquid spray, collagen preparation, gel, semisolid gel, or ointment. In some embodiments, the transdermal composition may be used "as is" or impregnated onto a breathable film such as polyurethane or nonwoven material or a dermal patch, or skin patch. In other embodiments the transdermal composition is combined with substances that increase the drug ability to penetrate the skin by drug solubilization and/or by affecting the skin biological structure that opens the transdermal passages. Typical penetration enhancers are e.g. isopropyl myristate, oleic alcohol, oleic acid, lauric acid, isopropyl palmitate, ester of fatty acids, DMSO.

In embodiments of the present invention the composition may include acid or base components. As used herein, the term "component" is intended to include those naturally occurring compounds and molecules identified as well as those formulated such as but not limited to pharmaceutically acceptable salts, esters, and combinations thereof. For example, when an acidic substituent, such as —COOH, is present, the ammonium, sodium, potassium, calcium and like salts, are contemplated as possible embodiments for administration to a biological host. When a basic group such as amino or a basic heteroaryl radical, such as pyridyl is present, then an acidic salt, such as hydrochloride, hydrobromide, acetate, maleate, palmoate, phosphate, methanesulfonate, p-toluenesulfonate, and the like, is contemplated as a possible form for administration to a biological host.

Similarly, where an acid group is present, then pharmaceutically acceptable esters of the compound e.g., methyl, tert-butyl, pivaloyloxymethyl, succinyl, and the like are contemplated as possible forms of the compounds, such esters being known in the art for modifying solubility and/or hydrolysis characteristics for use as sustained release or prodrug formulations. In addition, some components may form solvates with water or common organic solvents. Such solvates are contemplated as part of the present invention as well.

Aqueous suspensions may contain the components or active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, and one or more agents, such as sucrose.

Oily suspensions may be formulated by suspending the components in a vegetable oil, for example arachis oil, olive oil, sesame oil or coconut oil, or in a mineral oil or in a carrier such as liquid paraffin. The oily suspensions may contain a thickening agent, for example beeswax, hard paraffin or acetyl alcohol. Other thickeners may include hydroxy methyl cellulose, hydroxylpropyl cellulose, hydroxylethyl cellulose polyacrylic acid, and/or, sodium carboxy methyl cellulose.

Dispersible powders and granules suitable for preparation of an aqueous suspension by the addition of water provide the active composition admixture with a dispersing or wetting agent, suspending agent and one or more preservatives. Suitable dispersing or wetting agents and suspending agents are exemplified by those already mentioned above.

One embodiment of the composition may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate.

One embodiment of the composition may also be in the form of suppositories for rectal administration of the composition. These compositions can be prepared for example by mixing the composition with a suitable non-irritating excipient that is solid at ordinary temperatures but liquid at the rectal temperature and will therefore melt in the rectum to release the drug. Such materials are cocoa butter and polyethylene glycols, for example.

Formulations of the compositions useful for practicing the present invention may be prepared for storage by mixing the selected composition having the desired degree of purity with optional physiologically pharmaceutically-acceptable carriers, excipients, or stabilizers in the form of a lyophilized cake or an aqueous solution. (Remington's Pharmaceutical Sciences, 18th edition, A. R. Gennaro, ed., Mack Publishing Company (1990)).

Embodiments of the composition may be sterile. This is accomplished by filtration through sterile filtration membranes, prior to or following lyophilization and reconstitution. One embodiment of the composition for parenteral administration ordinarily will be stored in lyophilized form or in solution.

Embodiments of the composition may be placed into a container having a sterile access port, for example, an intravenous solution bag or vial having a stopper pierceable by a hypodermic injection needle. The route of administration of the composition is in accord with known methods, e.g. topical, or by sustained release systems or imtreeation devices.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman, et al., Biopolymers, 22: 547-556 (1983), poly (2-hydroxyethyl-methacrylate) (Langer, et al., J. Biomed. Mater. Res., 15:167-277 (1981) and Langer, Chem. Tech., 12:98-105 (1982), ethylene vinyl acetate (Langer, et al., supra) or poly-D(-)-3-hydroxybutyric acid (EP 133,988). Sustained-release compositions also may include liposomes, which can be prepared by any of several methods known in the art (e.g., DE 3,218,121; Epstein, et al., Proc. Natl. Acad. Sci. USA, 82:3688-3692 (1985); Hwang, et al., Proc. Natl. Acad. Sci. USA, 77:4030-4034 (1980); EP 52,322; EP 36,676; EP. 88,046; EP 143,949).

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope of the present invention. Those with skill in the art will readily appreciate that embodiments in accordance with the present invention may be implemented in a very wide variety of ways. This application is intended to cover any adaptations or variations of the embodiments discussed herein. Therefore, it is manifestly intended that embodiments in accordance with the present invention be limited only by the claims and the equivalents thereof.

All citations contained herein are incorporated in their entireties by reference.

What is claimed is:

1. A transdermal patch for induction therapy used with a monoclonal antibody treatment, the patch comprising:
   a first reservoir for containing a first component;
   a first microporous membrane in fluid communication with the first reservoir, the first membrane having a first porosity;
   a second reservoir for containing a second component;
   a second microporous membrane in fluid communication with the first reservoir, the second membrane having a second porosity;
   wherein the first component comprises a DNA and histone hypomethylating agent in a first transdermal composition and the second component comprises a histone deacetylase inhibitor (HDACi) in a second transdermal composition;
   wherein the first porosity and the first transdermal composition are selected to transfer an effective amount of the DNA and histone hypomethylating agent across the first membrane over a first desired period of time, and the second porosity and the second transdermal composition are selected to transfer an effective amount of the HDACi across the second membrane over a second desired period of time;
   wherein the first and second microporous membranes define a plurality of holes having a diameter of about 0.05 to about 10 micrometers, to form the first and second porosities; and
   wherein the transdermal patch delivers 5-20 mg/m$^2$ of histone hypomethylating agent and 10-20 mg/m$^2$ of HDACi per day.

2. The transdermal patch of claim 1, wherein the first porosity and the second porosity are substantially the same.

3. The transdermal patch of claim 1, wherein the first desired period of time and the second desired period of time are substantially the same.

4. The transdermal patch of claim 1, further comprising an impermeable membrane that separates the first reservoir from the second reservoir.

5. The transdermal patch of claim 1, wherein the DNA and histone hypomethylating agent is cladribine and wherein the patch delivers about 5-15 mg/m$^2$ of cladribine per day.

6. The transdermal patch of claim 1, wherein the HDACi is entinostat and wherein the patch delivers about 10-20 mg/m$^2$ of entinostat per day.

7. The transdermal patch of claim 1, wherein the DNA and histone hypomethylating agent is cladribine and wherein the patch delivers about 20-100 mg/m$^2$ of cladribine over five days.

8. The transdermal patch of claim 1, wherein the patch delivers about 40-80 mg/m$^2$ of HDACi over five days.

9. The transdermal patch of claim 8, wherein the HDACi is entinostat.

10. A method of induction therapy used with a monoclonal antibody in a treatment in a patient in need thereof comprising administering to the patient the transdermal patch of claim 1.

11. The method of claim 10, wherein the hypomethylating agent is cladribine.

12. The method of claim 11, wherein the HDACi comprises romidepsin, entinostat, belinostat, panobinostat or a combination thereof.

13. The method of claim 12, wherein the cladribine is administered in an amount of about 5-20 mg/m$^2$.

14. The method of claim 13, wherein the HDACi is administered in an amount of about 10-20 mg/m$^2$.

15. The method of claim 10, wherein the cladribine is administered in an amount of about 5-20 mg/m$^2$ and the HDACi is administered in an amount of about 10-20 mg/m$^2$.

16. The method of claim 10, wherein the hypomethylating agent is cladribine administered in an amount of about 5-20 mg/m$^2$ and the HDACi is entinostat administered in an amount of about 10-20 mg/m$^2$.

* * * * *